(12) United States Patent
Shih et al.

(10) Patent No.: US 8,574,432 B2
(45) Date of Patent: Nov. 5, 2013

(54) INTEGRATED CHROMATOGRAPHY DEVICES AND SYSTEMS FOR MONITORING ANALYTES IN REAL TIME AND METHODS FOR MANUFACTURING THE SAME

(75) Inventors: Chi-yuan Shih, Pasadena, CA (US); Yu-Chong Tai, Pasadena, CA (US); Jun Xie, Foster City, CA (US); Darron K. Young, South Pasadena, CA (US); Po-Jui Chen, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 980 days.

(21) Appl. No.: 11/404,496

(22) Filed: Apr. 14, 2006

(65) Prior Publication Data

US 2007/0000838 A1   Jan. 4, 2007

Related U.S. Application Data

(60) Provisional application No. 60/671,309, filed on Apr. 14, 2005, provisional application No. 60/673,272, filed on Apr. 20, 2005.

(51) Int. Cl.
*B01D 15/08* (2006.01)
*G01N 30/02* (2006.01)
*C02F 1/28* (2006.01)

(52) U.S. Cl.
USPC ......... 210/198.2; 210/656; 422/70; 73/61.52; 73/61.53

(58) Field of Classification Search
USPC ............................................. 210/656, 198.2
See application file for complete search history.

(56) References Cited

U.S. PATENT DOCUMENTS

| | | | |
|---|---|---|---|
| 6,287,831 B1 | 9/2001 | Tai et al. | |
| 6,534,295 B2 | 3/2003 | Tai et al. | |
| 6,936,167 B2 * | 8/2005 | Hobbs et al. | 210/198.2 |
| 6,945,116 B2 | 9/2005 | Xie et al. | |
| 7,217,367 B2 * | 5/2007 | Huang et al. | 210/656 |
| 2002/0139751 A1 | 10/2002 | Zhang et al. | |
| 2003/0027354 A1* | 2/2003 | Geli | 436/178 |
| 2003/0186430 A1 | 10/2003 | Tai et al. | |
| 2004/0089607 A1 | 5/2004 | Hobbs et al. | |
| 2004/0124085 A1 | 7/2004 | Tai et al. | |
| 2005/0051489 A1 | 3/2005 | Tai et al. | |
| 2005/0274174 A1 | 12/2005 | Tai et al. | |
| 2006/0007983 A1 | 1/2006 | Tai et al. | |
| 2006/0018360 A1 | 1/2006 | Tai et al. | |
| 2006/0057597 A1 | 3/2006 | Tai et al. | |

OTHER PUBLICATIONS de Boer et al. Micromachining of buried micro channels in silicon. Journal of Microelectromechanical Systems. vol. 9, No. 1 (Mar. 2000) pp. 94-103.*
Wu et al. Deposition of high purity parylene-F using low pressure low temperature chemical vapor deposition. Journal of Electric Materials. Vo.l 26, No. 8 (1997) pp. 949-953.*
PCT International Search Report for PCT/US06/14239, Oct. 2006.

* cited by examiner

*Primary Examiner* — Katherine Zalasky
(74) *Attorney, Agent, or Firm* — Kilpatrick Townsend & Stockton LLP (57) ABSTRACT

Systems and methods for monitoring analytes in real time using integrated chromatography systems and devices. Integrated microfluidic liquid chromatography devices and systems include multiple separation columns integrated into a single substrate. Using such a device, parallel analysis of multiple samples can be performed simultaneously and/or sequential analysis of a single sample can be performed simultaneously on a single chip or substrate. The devices and systems are well suited for use in high pressure liquid chromatography (HPLC) applications. HPLC chips and devices including embedded parylene channels can be fabricated using a single mask process.

20 Claims, 8 Drawing Sheets

Fabricated single-mask HPLC chip

FIG. 3A thin-film (skin) HPLC device by
peeling parylene membrane from (a)

FIG. 3B cross-section of embedded parylene channel

FIG. 3C

FIG. 4A  15 µm parylene coating process filter/column section

FIG. 4B  15 µm parylene coating process filter/column section

FIG. 4C  15 µm parylene coating process liquid inlet/outlet

FIG. 4D  15 µm parylene coating process liquid inlet/outlet

XeF2 etching efficiency study. 18 loops of XeF2 etching were used on a single wafer.

FIG. 5

Illustration from SEM picture of LIF detector channel profile. Parylene/oxide layer was removed.

FIG. 6

5μm fluorescent beads were packed into an embedded parylene column by slurry-packing.

FIG. 7

Embedded parylene channel loaded with 1015 psi inner pressure without fracture.

System packaging for chromatography and LIF detection

INTEGRATED CHROMATOGRAPHY DEVICES AND SYSTEMS FOR MONITORING ANALYTES IN REAL TIME AND METHODS FOR MANUFACTURING THE SAME

CROSS-REFERENCES TO RELATED APPLICATIONS

This application claims the benefit of U.S. Provisional Application No. 60/671,309, filed Apr. 14, 2005 for "INTEGRATED CHROMATOGRAPHY DEVICES AND SYSTEMS FOR MONITORING ANALYTES IN REAL TIME," and 60/673,272, filed Apr. 20, 2005 for "AN EMBEDDED-PARYLENE-CHANNEL TECHNOLOGY FOR LIQUID CHROMATOGRAPHY APPLICATIONS," the disclosures of which are incorporated herein by reference in their entirety.

STATEMENT AS TO RIGHTS TO INVENTIONS MADE UNDER FEDERALLY SPONSORED RESEARCH OR DEVELOPMENT

The government may have certain rights to the invention based on National Institute of Health Grant No. 5R01 RR06217-10 and National Science Foundation Grant EEC-9402726.

BACKGROUND OF THE INVENTION

This invention relates to devices and systems for chromatography and, more specifically, to devices and systems that use an integrated microfluidic chip for sample preparation, separation and detection of analytes in real time.

There are three general types of chromatography systems, gas chromatography (GC), liquid chromatography (LC) and supercritical fluid (SFC). Chromatography is an analytical technique for the separation and determination of organic and inorganic solutes in any samples especially biological, pharmaceutical, food, environmental, industrial, etc. In a liquid chromatographic process, for example, a liquid permeates through a porous solid stationary phase and elutes the solutes into a flow-through detector. The stationary phase is usually in the form of small-diameter (5-10 mm) uniform particles, packed into a cylindrical column. The typical column is constructed from a rigid material (such as stainless steel or plastic) and is generally 5-30 cm long and the internal diameter is in the range of 1-9 mm.

With the advent of micromaching techniques and other processes for fabricating microscale and sub-microscale devices, it has become possible to create integrated chromatography systems and devices.

BRIEF SUMMARY OF THE INVENTION

The present invention provides systems and methods for monitoring analytes in real time using integrated chromatography systems and devices. The devices and systems are well suited for use in high pressure liquid chromatography (HPLC) applications. In one aspect, the present invention also provides HPLC chips and devices as well as methods for fabricating HPLC chips and devices using a single mask process.

One aspect of the invention provides an integrated microfluidic liquid chromatography device that includes multiple separation columns integrated into a single substrate, such as for example a silicon wafer or chip. Using such a device, parallel analysis of multiple samples can be performed simultaneously and/or sequential analysis of a single sample can be performed simultaneously on a single chip or substrate.

One embodiment provides an integrated microfluidic chromatography device comprising: a substrate having a surface; a first separation column integrated into the substrate surface and adapted to perform a first chromatographic separation on a first sample; a second separation column integrated into the substrate surface and adapted to perform a second chromatographic separation on a second sample, wherein the first and second samples may be the same or different; wherein the first chromatographic separation is of a different type than the second chromatographic separation. The system is not limited to two samples, but larger numbers of samples can be analyzed. The chromatography can be a liquid chromatrography. The first and second samples can be derived from the same larger sample which can be split into any number of portions including first and second portions to provide first and second samples.

In one embodiment of the invention, the separation columns include columns adapted to perform different types of chromatographic separations, such that different types of chromatography can be performed simultaneously or sequentially on the same chip. The type of chromatography is not particularly limited. For example, each of the multiple separation columns may be adapted to perform a type of chromatography independently selected from, for example, reversed-phase, normal-phase, size-exclusion, ion-exchange and affinity chromatography. The different separation columns may be arranged in a parallel alignment, such that two or more different samples (or two or more different portions of a single sample) may be independently subjected to different chromatographic separations. Alternatively, the different separation columns may be arranged in series, such that the chromatographic separations are coupled.

In one embodiment of the invention the microfluidic device includes multiple detectors connected to and in fluid communication with each separation column. The detectors can be microscale or nanoscale and can include electrochemical, mechanical, or optical detectors. In a preferred embodiment, arrays of microfabricated electrochemical detectors can be integrated into the substrate and can be used to detect analytes coming off the various microfluidic separation columns.

In another embodiment a chromatographic method is provided for separating analytes in a sample, the method comprising introducing a first sample into a first separation column integrated into a substrate to perform a first chromatographic separation and introducing a second sample into a second separation column integrated into the substrate to perform a second chromatographic separation, wherein the first and second samples can be the same or different, and wherein the first chromatographic separation is of a different type than the second chromatographic separation. The first and second samples can be derived from the same larger sample which can be split into any number of portions including first and second portions to provide first and second samples.

In another embodiment, an integrated microfluidic liquid chromatography device is provided that typically includes a substrate having a surface; at least two separation columns each having an inlet and an outlet, the at least two separation columns integrated into the substrate surface and adapted to perform a chromatographic separation on a sample; and a detector array comprising at least two sample detectors integrated into the substrate and in fluid communication with the outlet of the at least two separation columns.

In a further embodiment, a chromatographic method is provided for analyzing analytes in a sample. The method typically includes introducing the sample into at least one separation column integrated into a substrate to perform at least one chromatographic separation on the sample and passing the separated sample into a detector array comprising at least two sample detectors integrated into the substrate. Multiple separation columns can be used in series or parallel.

In another embodiment, a microfluidic system for sample analysis is provided. The system typically includes a reservoir assembly comprising at least one sample reservoir; an integrated microfluidic chromatography device in fluid communication with the at least one sample reservoir, the integrated microfluidic chromatography device comprising at least two separation columns integrated into a substrate and at least one detector integrated into the substrate; a pump adapted to deliver the sample from the at least one reservoir to the integrated microfluidic chromatography device; an analyte detection assembly comprising at least one detector in fluid communication with the at least one separation column; and a processing unit in electrical communication with the at least one detector.

Another aspect of the invention provides a portable microfluidic system for sample analysis. The system desirably has dimensions that make it suitable as a hand-held instrument for various analytical applications. For example, the largest lateral dimension such as length or width can be 12 inches or less, or even 6 inches or less, or even 2 inches or less. The system can include a reservoir assembly comprising at least one reservoir for holding a sample of interest and, optionally, additional reservoirs for holding buffers and/or eluent solvents. The system can further include a microfluidic liquid chromatography device comprising at least one separation column integrated into a substrate and in fluid communication with the reservoirs of the reservoir assembly. The microfluidic chromatography device also desirably includes at least one detector in fluid communication with the at least one separation column. In a preferred embodiment, the microfluidic liquid chromatography device is an integrated microfluidic chip that includes multiple separation columns and multiple detectors, as described in the preceding paragraphs. The portable microfluidic system further can include at least one pump disposed on the substrate for delivering sample, buffer and/or eluent solvent to one of the separation columns on the substrate. In one embodiment, the pump is an electrochemical pump. A processing unit in electrical communication with the detectors can be also provided. This processing unit (e.g., a central processing unit in a computer) can collect and store data related to various analytes from the detectors.

The portable microfluidic system may further optionally include one or more of the following components. The system, for example, may include a control unit in electrical communication with the processing unit and the reservoir assembly. This control unit can include a feedback loop that allows the amount of sample, buffer and/or eluent solvent leaving the reservoirs to be adjusted based on the data collected by the processing unit. The system may include a display device in electrical communication with the processing unit for displaying data collected by the processing unit. The system may include a wireless communication system in communication with the processing unit for transmitting data from the processing unit to a remote location. The system is desirably housed in a housing having dimensions that make it easy for an individual to transport the system from location to location in his or her hands.

The portable microfluidic system may be tailored to monitor and record a broad spectrum of target analytes. In one embodiment, the system is designed to analyze water from oceans, rivers, aqueducts, or households. In another embodiment the system is adapted to monitor food quality. In yet another embodiment the system is adapted to analyze bodily fluids for clinical diagnostics and testing, including but not limited to, urine, blood, and saliva. In another embodiment, the system is adapted for use in the process of drug discovery.

According to yet a further aspect of the present invention, a method is provided for forming embedded filter and column sections in a chromatography device. The method typically includes providing a substrate, forming an oxide layer on a first side of the substrate, and etching the oxide layer using a single mask to expose the substrate and define device features including a filter section adjacent a separation column section, wherein a width of a channel defining the filter section is narrower that a width of a channel defining the column section. The method also typically includes etching the defined device features, depositing a layer of parylene in the filter and column channels for a period of time sufficient to seal the narrower filter channel, and after the filter channel has been sealed, continuing to deposit parylene, wherein parylene diffuses into the enclosed filter channel from the adjacent column channel region thereby reducing a cross-sectional dimension of the filter channel. In certain aspects, parylene C is used during the deposition steps. In certain aspects, one or more additional masks to define additional device features. Also, in certain aspects, a layer of parylene including the device features is formed on the substrate, wherein the method further typically includes removing the parylene layer from the substrate so as to provide a thin-film parylene device comprising the device features.

According to yet another aspect of the present invention, a chromatography device having one or more embedded parylene channels is provided. The device typically includes a substrate, at least one channel region etched into the substrate, and an embedded parylene channel formed in the channel region by depositing parylene on the substrate for a period of time sufficient to form walls in the at least one channel region and to seal the channel region and define an inner channel. In certain aspects, the first sub-region includes a filter section of the chromatography device and the second sub-region includes a column separation section of the chromatograph device. In certain aspects, the channel region includes a first sub-region and a second sub-region, the first sub-region having a narrower width and/or depth than the second sub-region, wherein a cross-sectional dimension of the inner channel of the first sub-region is smaller than a cross-sectional dimension of the inner channel of the second sub-region.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

Figure 1:
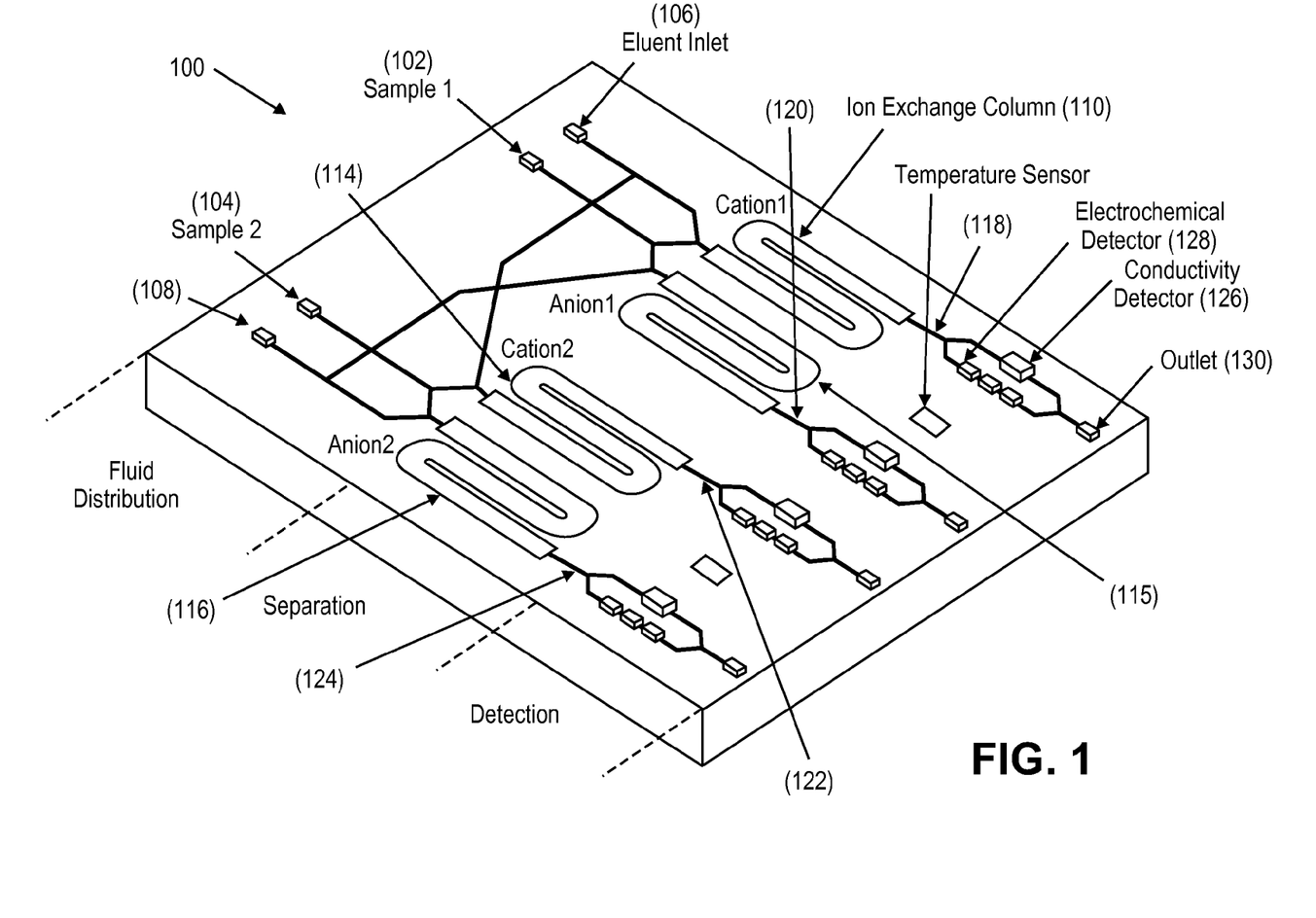
FIG. 1 shows a schematic diagram of a microfluidic liquid chromatography device that uses two types of ion chromatography to analyze two different samples.

FIG. 1 shows a microfluidic liquid chromatography device 100 in accordance with an embodiment of the present invention. Throughout much of this description, FIG. 1 will be used to illustrate aspects and embodiments the invention. However, it should be understood that the invention is not limited to the particular aspects and embodiments depicted in FIG. 1.

In certain aspects, the microfluidic substrates, or "chips", that are the basis for the devices and systems provided herein typically include integrated components having one or more dimensions on the order of millimeters (mm) (e.g., 10 mm or less), micrometers (e.g., 10 micrometers or less) or even nanometers (e.g., 100 nm or less) and are typically integrated into a surface of the substrate using micromachining techniques, such as lithography (e.g., photolithography), etching, sputtering and chemical vapor deposition.

Multiple Separation Columns on a Single Substrate

The microfluidic liquid chromatography device 100, in one aspect, includes a substrate having a surface and a plurality of separation columns integrated into or on the substrate surface, wherein at least two separation columns are adapted to perform a different type of chromatographic separation on one or more samples of interest. The substrate may be made of a variety of materials including, but not limited to, silicon, glass, metal, and plastic, and combinations thereof. In one aspect, each separation column includes an inlet, an outlet, a microchannel defined between the inlet and the outlet and a solid phase packed within the microchannel. Descriptions of suitable microfluidic separation columns and methods for fabricating them on a substrate may be found, for example, in U.S. patent application Ser. No. 10/917,257 filed Aug. 11, 2004, "Design of an IC-Processed Polymer Nano-Liquid Chromatography System On-a-Chip and Method of Making It" (abandoned); U.S. provisional patent application Ser. No. 60/586,576 filed Jul. 9. 2004, "Integrated LC-ESI On A Chip" (expired); U.S. nonprovisional 11/059,625 filed Feb. 17, 2005, "On-Chip Temperature Controlled Liquid Chromatography Methods and Devices" (pending issue on May 12, 2009 as U.S. Pat. No. 7,530,259, the entire disclosures of which are incorporated herein by reference. In certain aspects, single mask technology as discussed below is used to fabricate devices and chips including one or multiple separation columns and other device features as described herein.

The separation columns may be arranged in parallel such that multiple samples and/or multiple portions of a single sample may be subjected to one or more column separations, desirably simultaneously, on a single integrated chip. For certain samples, multi-dimensional separation may be desirable. In this situation, multiple on-chip separation columns can be coupled together in series to perform multi-dimensional separation. For example, an ion-exchange column can be coupled to a reverse-phase column for protein separation. In some devices some of the separation columns can be arranged in a parallel alignment on a substrate while others can be arranged in a serial alignment on the substrate.

Liquid chromatography generally involves the separation of analytes as they travel through the column in liquid rather than gas phase. See, for example, Meyer, V. (1998). *Practical high-performance liquid chromatography*. Chichester; N.Y., Wiley. A variety of different types of separation columns may be employed in the present microfluidic devices. These columns include, but are not limited to reversed-phase, normal-phase, size-exclusion, ion-exchange, and affinity chromatography columns.

In normal-phase liquid chromatography, the stationary phase is more polar than the mobile phase. For example, the stationary phase might be bonded siloxane with a polar functional group, and the mobile phase is a nonpolar organic solvent (such as n-hexane, methylene chloride, or chloroform).

In reverse-phase liquid chromatography, which is now one of the most common forms of liquid chromatography, the stationary phase is less polar than the mobile phase. For example, methanol, acetonitrile, water, or mixtures of these solvents can be used as the mobile phase.

Size-exclusion chromatography, also known as gel-filtration or gel-permeation chromatography, uses porous particles to separate molecules by size. Smaller-sized molecules enter the particles and take longer to pass through the column than larger size molecules that cannot enter the particles.

In ion-exchange chromatography, charged substances are separated by materials in the column that carry an opposite charge. For example, the ionic groups of exchange columns are covalently bound to a gel matrix, and small concentrations of counter ions are present in the buffer. When a sample is introduced to the column, an exchange with the weakly bound counter ions takes place and causes separation.

Affinity chromatography makes use of biological interactions in the column to separate molecules. For example, antibodies can be used to bind with antigens, or enzymes can be used to bind with inhibitors.

In the embodiment shown in FIG. 1, the microfluidic chromatography device 100 is an integrated microfluidic chip that includes three sections: 1) a fluid distribution section; 2) a separation section; and 3) an analyte detection section. The fluid distribution section can include multiple inlet lines, e.g., two sample inlet lines 102, 104 as shown, for introducing samples of interest into the device and for conducting the sample to the separation region of the device, and two eluent inlet lines 106, 108 for providing eluent to the sample. The separation section includes four separation columns designed to perform two different separations on each of two different samples. The column inlet of each separation column can be in fluid communication with one sample inlet line and one eluent inlet line. The first and third separation columns 110, 114 can be, for example, cation exchange columns connected in parallel and can be adapted to receive sample and eluent from the sample inlet lines and the eluent inlet lines. Similarly, the second and fourth columns 115, 116 can be anion exchange columns connected in parallel and can be adapted to receive sample and eluent from the sample inlet lines and the eluent inlet lines. Using this construction, both organic and inorganic anions and cations in each sample can be separated and detected (e.g., as described below) on the same chip.

Although the exemplary embodiment shown in FIG. 1 utilizes ion-exchange chromatography columns, other types of chromatography columns may be employed. For example, in another embodiment, the microchannels of the separation columns may include a solid phase that is modified specifically to perform certain applications. In particles that are normally used as solid phase, a monolith solid phase can be integrated in the separation column.

Arrays of Detectors

Once the sample has undergone chromatographic separation, the analytes may be directed into a variety of different detectors for analysis. In one embodiment, an array of multiple detectors are connected to each separation column, where each array includes at least two different kinds of detectors. The detectors can be microscale or nanoscale detectors and are desirably integrated into the same substrate as the separation columns such that they form part of a single integrated microfluidic chip. Sensors in these size regimes have faster response time, higher sensitivity, and lower detection limits than their larger counterparts. Suitable detectors include electrochemical, mechanical, and optical detectors.

The detectors in the detector array are in fluid communication with the outlet of one or more separation columns such that analyte molecules eluted from the column or columns are directed into, over or across the detector or a detection region for analysis.

In an exemplary embodiment, the microfluidic liquid chromatography device includes at least one detector array composed of microfabricated electrochemical detectors to detect analytes. Suitable electrochemical detectors include potentiometric, amperometric, and conductometric detectors. Potentiometric detectors measure a change in potential on their surface relative to a reference electrode. Amperometric detectors function by the production of a current when a potential is applied between two electrodes. Conductometric detectors rely on changes of electric conductivity of a film or bulk material in a flow cell where the conductivity is affected by the presence of analytes.

In some embodiments, interdigitated microscale or nanoscale electrodes disposed inside a flow channel in fluid communication with the outlet of one or more separation columns may be used as the electrochemical sensors. In one illustrative embodiment, an array of amperometric detectors may be placed inside a flow channel. Each detector can work alone to detect individual analytes or work in conjunction with other detectors to provide necessary reference or calibration information. For example, each detector can be set to work in a different "zone" (working potential), providing a third dimension of information (the potential axis).

The electrodes in the electrochemical detectors may be made of various materials, including but not limited to, carbon or platinum. For example, U.S. nonprovisional patent application, Ser. No. 11/040,116 filed Jan. 24, 2005, Pyrolyzed Thin-Film Carbon (pending) and U.S. nonprovisional patent application, Ser. No. 10/973,938 filed Oct. 25, 2004, "Pyrolyzed-Parylene Based Sensors and Method of Manufacture," (issued Jul. 3, 2007 as U.S. Pat. No. 7,238,941) disclose carbon electrodes made of pyrolized parylene that may be used in electrochemical detectors in accordance with the present invention. The entire disclosures of both references are incorporated herein by reference.

In other embodiments, an optical detection mechanism, such as UV and visible absorption or fluorescence, can be utilized. In these embodiments, an optical detector and light source may be integrated onto the substrate or coupled to the substrate externally.

Each array of detectors can be inserted between the separation column and other arrays of detectors. Because the dead volume can be as small as 1 nL, there is little band broadening.

In the embodiment shown in FIG. 1, the outlet of each of the four separation columns is in fluid communication with a flow channel 118, 120, 122, 124 and each flow channel is split into two flow paths arranged in a parallel alignment. A first type of detector 126 (e.g., a conductivity detector) is disposed along one path of the flow channel and at least one second type of detector 128 is disposed along the second path of the flow channel. After passing through the detectors, the sample continues to flow to a flow channel outlet 130 where it may pass out of the integrated microfluidic chip for collection or further analysis.

In addition to the one or more separation columns and the one or more detectors, the integrated microfluidic chips may include additional components for preprocessing samples and for directing and controlling the flow of fluids between chip components. Such additional components include, but are not limited to, filters, valves, pumps, mixing chambers, and sample injectors. Such components and methods for building them into a microfluidic chip are described in U.S. Patent Publication No. 2004/0124085 and U.S. Provisional Patent Application Ser. No. 60/586,576 (expired), the entire disclosures of which are incorporated herein by reference.

Portable, HPLC-Based Instrument For Real Time Monitoring

Figure 2:
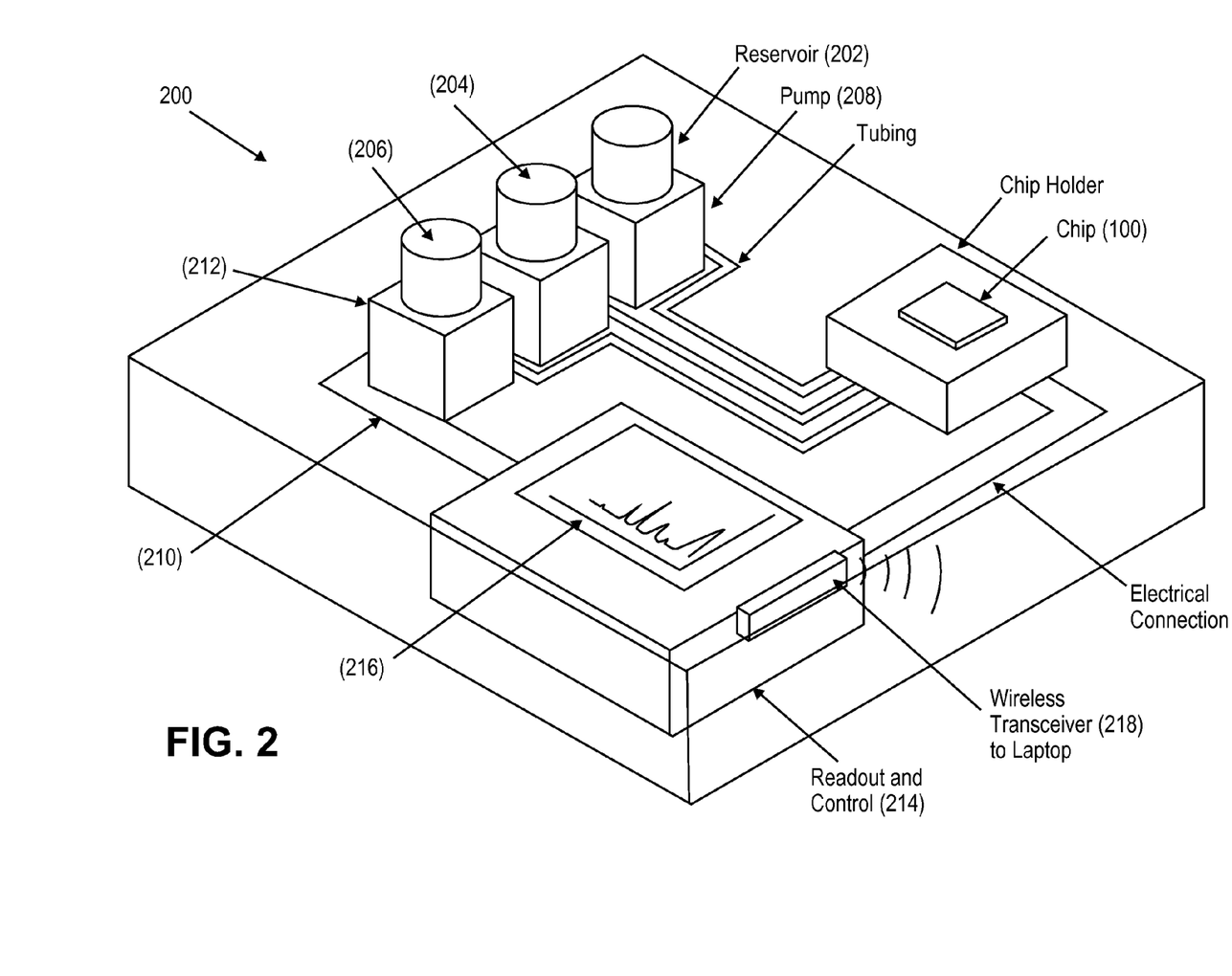
FIG. 2 shows a portable integrated microfluidic chip-based system in accordance with the present invention.

Another aspect of the invention provides a portable system for analyzing samples for various applications. The system is typically contained within a housing and desirably has dimensions that render it suitable for transportation from one location to another in a users hands (i.e., it may be a "handheld" device) or in a briefcase or backpack or other carrying case or device. For example, the perimeter around the device in two dimensional lateral space can be, for example, 24 inches or less, or more particularly, 12 inches or less. FIG. 2 shows a portable integrated-microfluidic chip-based system in accordance with one embodiment of the present invention. In the following description, FIG. 2 will be used to illustrate the invention. However, it should be understood that the invention is not limited to the particular embodiment depicted in FIG. 2.

The system can include a microfluidic chip adapted to separate and analyze analytes in a sample. For example, the system may include an integrated microfluidic chip having multiple separation columns and/or multiple detectors, as previously described herein with reference to FIG. 1. In certain aspects, the system also includes a reservoir apparatus having at least one sample reservoir for holding a sample and desirably at least one additional reservoir for holding a buffer and/or eluent. The reservoirs in the reservoir assembly can be in fluid communication (e.g., through tubing) with the inlets of one or more separation columns on the integrated microfluidic chip. Several reservoirs with mL volume may be used to store solvents or buffers. Due to the small fluid volume used in a typical test (~10s μL), the solvents or buffers in the reservoirs can be used for multiple, e.g., from a few to more than 100, tests.

The samples, buffers and eluents may be delivered from the reservoirs to the separation columns with the help of one or more pumps. In one embodiment, the system includes a pump based on commercially available components that is external to the integrated microfluidic chip. Normally such a pump can provide a flow rate down to 0.3μL/min and operate up to 100 psi. In another embodiment, for example when high pressure (typically ranging from 50 to 5000 psi) and low flow rate (typically ranging from 10 uL to 10 nL/min) are desired, an on-chip pumping system may be integrated into the microfluidic chip. For example, the electrochemical pump described in nonprovisional application Ser. No. 10/603,573 filed Jun. 34, 2003, Microfluidic Devices and Methods With Electrochemically Actuated Sample Processing (pending), the entire disclosure of which is incorporated by reference, may be used to precisely delivery sufficient pressure and a small flow rate. The electrochemical pump can also be easily miniaturized and integrated with the other components in the system. For example, the electrochemical pump can be directly integrated with the column as demonstrated in U.S. non-provisional application Ser. No. 60/586,576 filed Jul. 9, 2004, Integrated LC-ESI On A Chip (expired).

The system may also include a processing unit in electrical (including conductive and inductive) communication (e.g., through wires or coils) with the detectors of the integrated microfluidic chip. In certain aspects, the processing unit includes a microprocessor adapted to collect, process and store in a memory data regarding analytes from the detectors. The processing unit may be in electrical communication with a readout unit and/or a communication interface for transmitting data from the processor to a remote locations (e.g., to a remote computer). Suitable readout units include display devices, such as display screens (e.g., liquid crystal displays) and printers. Suitable communication interfaces include widely adopted wireless communication technologies well known in the art.

The system may also include a control unit in electrical communication with the processor and at least one other component of the system, such as a pump or a detector. For example, the control unit may use feedback to monitor and adjust the volume and/or flow rate of sample, buffer or eluent being delivered to the integrated microfluidic chip.

Another component that optionally may be included in the system is a flow sensor. The flow sensor can be integrated onto the chip or coupled to the chip. Suitable flow sensors and methods for building them into an integrated microfluidic chip are described in U.S. patent application Ser. No. 10/802,667 filed Mar. 16, 2004, Integrated Capacitive Microfluidic Sensors Method and Apparatus (issued Sept. 20, 2005 as U.S. Pat. No. 6,945,116), the entire disclosure of which is incorporated herein by reference. These flow sensors may be disposed along a liquid flow path, such as a sample inlet line to monitor flow and to provide feedback to other components such as pumps.

In a typical embodiment, a chip holder provides packaging for the integrated microfluidic chip and all fluidic/electrical connections from the other components to the chip. In a preferred embodiment, the chip holder and tubing are made of plastic materials, such as PEEK, due to its excellent chemical resistance and injection molding capability. If miniaturized pumping is needed, the reservoir assembly, including sample, buffer and/or eluent reservoirs may be contained on the chip holder which would provide sealing that might be necessary for certain operations.

In the embodiment shown in FIG. 2, the system 200 includes a reservoir assembly composed of three reservoirs 202, 204, 206, each of which has its own pump 208, 210, 212. Each reservoir is in fluid communication with an integrated microfluidic chip through a line of tubing. In one aspect, the integrated microfluidic chip is the microfluidic chromatography device 100 depicted in FIG. 1. The microfluidic chromatography device 100 is in electrical communication with processing unit 214 connected to a readout in the form of a display 216 and a wireless transceiver 218. The processing unit 214 is in electrical communication with the reservoir assembly, such that the processing unit is able to control the flow of sample, buffer and/or eluent from the reservoirs 202, 204, 206 to the microfluidic chromatography device 100.

Single Mask Fabrication

Figure 3A:
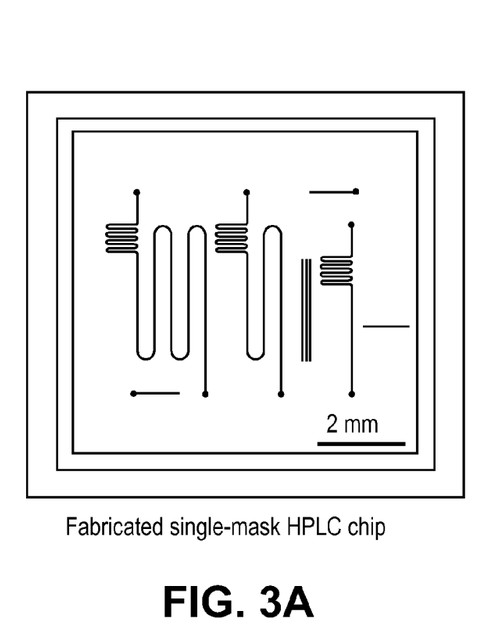
FIG. 3 illustrates (a) a HPLC chip fabricated according to a single mask process, (b) a thin-film HPLC device, and (c) an embedded parylene channel.
Figure 3B:
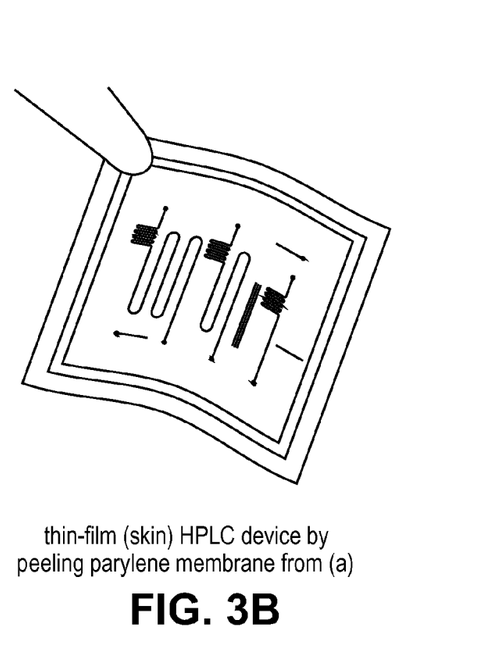
Figure 3C:
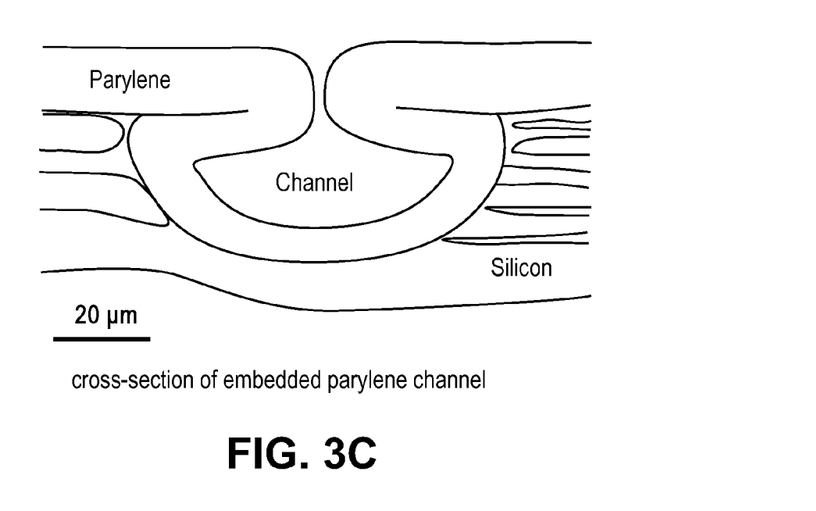

According to one embodiment, single mask processes are provided for producing embedded HPLC devices in a substrate. Such processes are particular useful for forming HPLC devices that require fluidic channel features and other device features that are able to withstand high pressures, and particularly higher pressures than are typically associated with gas phase chromatography systems. In certain aspects, parylene is used to form embedded channels in a substrate. In other aspects, a thin film device may be fabricated on a substrate and then removed, or "peeled" away. FIG. 3a shows an example of a HPLC chip fabricated using a single mask fabrication process according to one embodiment. FIG. 3b illustrates a thin-film device that has been removed from the substrate after fabrication, and FIG. 3c illustrates a cross section of an embedded parylene channel.

Figure 5:
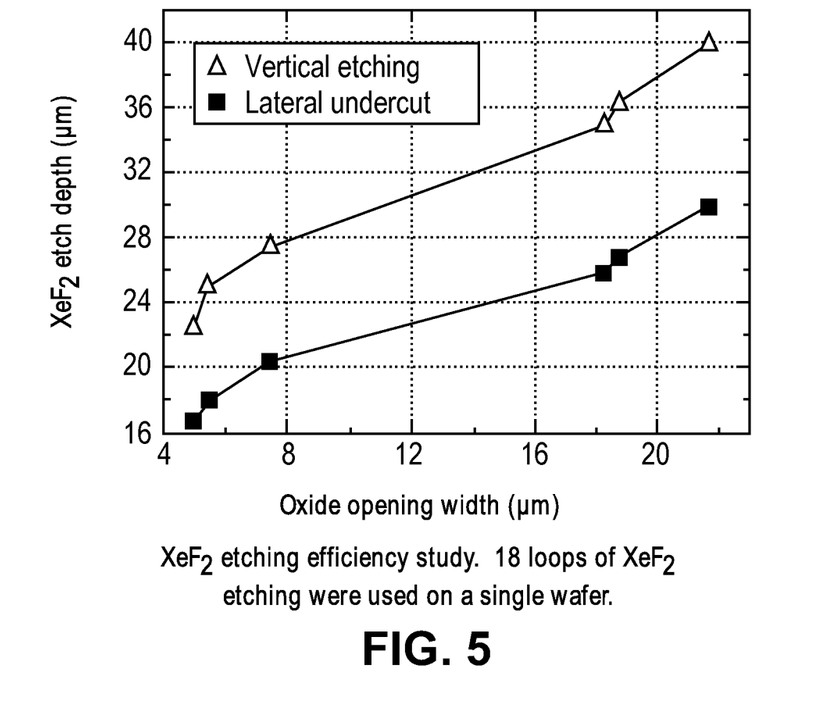
FIG. 5 shows an XeF$_2$ etching efficiency study.

According to one embodiment, a process for fabricating a chip or device begins by forming an oxide layer, e.g., 0.5 μm oxide (e.g., $SiO_2$), on one or both sides of a substrate or wafer. A useful substrate material includes silicon, e.g., a silicon wafer, although other materials such as glass, quartz, polymers, metals, ceramics and plastics can used for a substrate. The thickness of an oxide layer may range from about 0.1 μm to about 2.0 μm or greater, and oxide layers on different sides of the substrate need not have the same thickness. A first one of the oxide layers ("front side") is then patterned to define various chip features such as fluidic channels, liquid inlet/outlet ports, bead filter(s), separation column(s) and detection region(s) such as LIF detection cell patterns as are shown in FIG. 3. Patterning is preferably done using a single mask and an oxide etch, although more than one mask may be used. According to one aspect, for a silicon substrate, a buffered HF etch is used, although other oxide etch techniques may be used as are well known. After the front side has been patterned, the features are further processed by etching or otherwise forming the various channels and features of the device through the oxide openings. For a silicon substrate, for example, a $XeF_2$ etch (an isotropic gas phase silicon etching technique) is used to etch down and undercut silicon through oxide openings. Given that, due to mass transport limitations of $XeF_2$, the silicon etching rate is a function of oxide opening size, it is possible to control the size of features, e.g., channels and openings, for a given etch time by controlling the size of oxide openings defined by the mask(s). FIG. 5 shows an $XeF_2$ etching efficiency study. Thus, in certain aspects, control of desired feature sizes and dimensions is provided by controlling the size of the oxide openings.

In one embodiment, a layer of a material such as parylene is then conformally deposited or otherwise formed on the substrate front side, e.g., using a room-temperature CVD process, to form walls of fluidic channels and other features. Parylene is a USP Class VI biocompatible polymer that can be deposited through a highly-conformal vapor deposition process. Types of parylene include parylene C, F, A, AM, N, and D. Of the three most common types of parylene, parylene C is perhaps the most widely used in industry. The advantages of the use of parylene include its proven biocompatibility, its strength and flexibility (e.g., Young's modulus ≈4 GPa), its conformal pinhole-free room-temperature deposition, its low dielectric constant (≈3) and high volume resistivity (>$10^{16}$Ω-cm), its transparency, and its ease of manipulation using standard microfabrication techniques such as reactive ion etching (RIE). Although use of parylene, and in particular parylene-C, is preferred, one skilled in the art will understand that other useful materials such as other useful polymers, may be used to form channel walls.

Figure 4A:
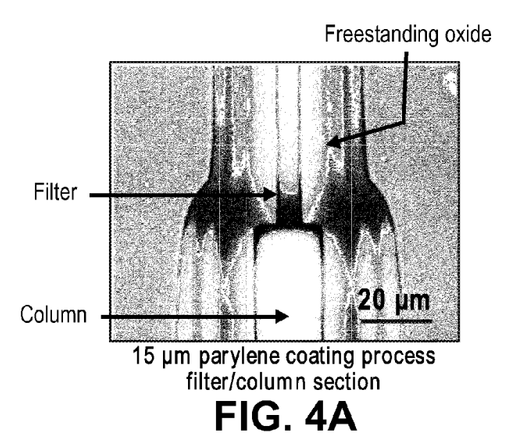
FIG. 4 shows an example of a parylene coating process for filter/column sections (a),(b), and for liquid inlet and outlet sections (c),(d).
Figure 4B:
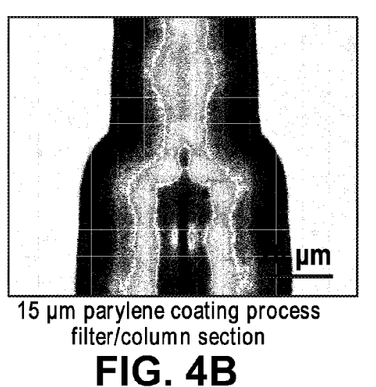
Figure 4C:
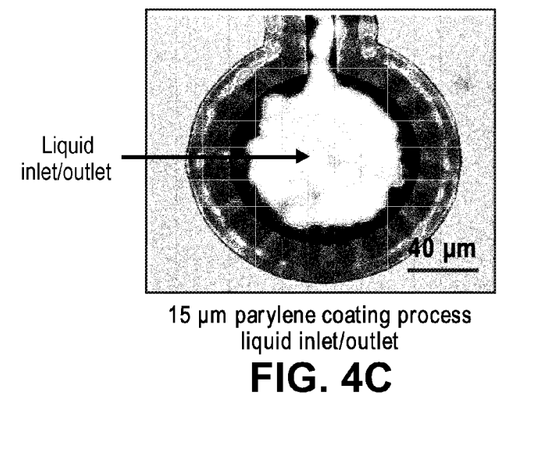
Figure 4D:
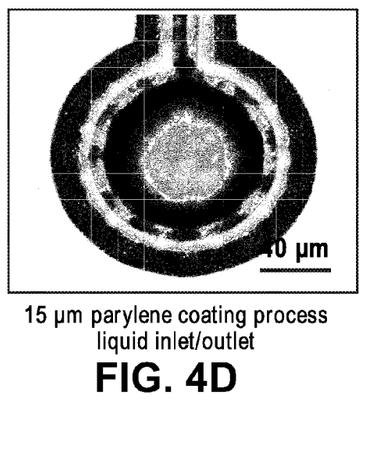

During the deposition process, due to the various oxide opening size differences of the various features, narrower openings are sealed faster than wider openings. For example, narrower column/filter sections are sealed from the top by parylene deposition but wider liquid inlet/outlet port features remain open as shown in FIG. 4. Also, narrower filter sections are sealed faster than wider column sections. As the deposition process continues, parylene penetrates and diffuses into the (enclosed) channels and those channels continue to be reduced in size. For example, as shown in FIGS. 4a and 4b, after the filter channel is sealed, parylene continues to diffuse into the filter channel through the still open column channel until the column channel is sealed. In this manner, it is possible to control the size of channels by also controlling the parylene deposition rate. For example, narrower features such as the bead-filter structure are formed by two mechanisms. First, due to mass transport limitation of $XeF_2$, the silicon etching rate is a function of oxide opening size (e.g., see FIG. 5). Therefore, a smaller oxide opening around the filter section, compared with the column section, results in a smaller $XeF_2$-etched channel cross-section. Second, after the oxide opening around the filter section is sealed by parylene deposition, the filter cross-section continues to shrink due to parylene diffusing into and coating its inner surface through the neighboring oxide opening of the column section. This is shown in FIG. 4.

Figure 6:
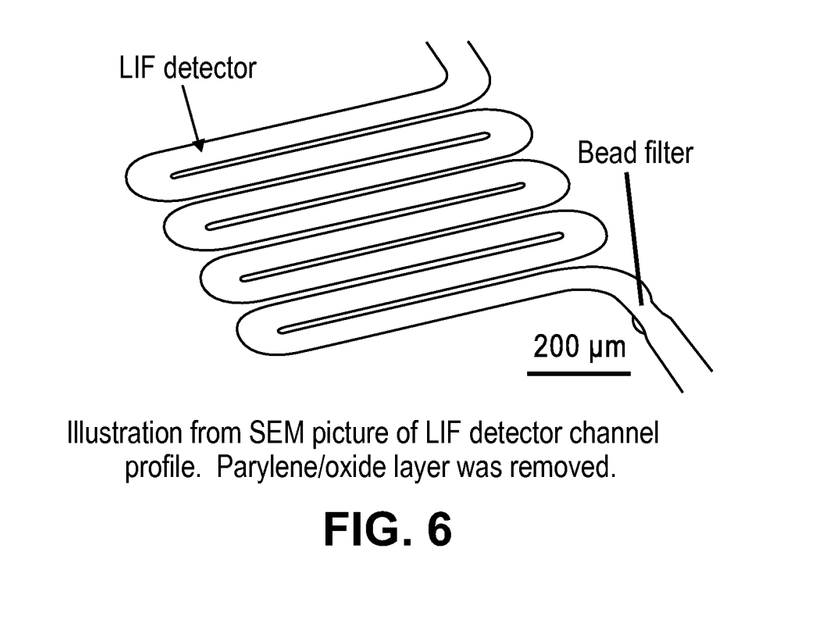
FIG. 6 shows a SEM picture of a LIF detector channel profile.

Any detection region type may be formed, however LIF detection is a desirable chromatography sensing mechanism due to its ease of incorporation, broad analyte species coverage and high sensitivity compared with UV absorption detection and other detection schemes. In one aspect, as shown in FIG. 6, an on-chip LIF detection cell is composed of closely-meandering fluidic channel matrix for convenient optical alignment. The recessed channel profile effectively enhances the LIF detection signal/noise ratio. Other useful detection regions types and features that can be formed on a device might include optical detection regions, electrical detection regions and devices, electrochemical detection regions and devices. In one aspect, multiple types of sensors and/or detection regions are provided on a device according to the present invention.

The single mask processes as described herein advantageously do not require a sacrificial photoresist layer. Also, the processes do not require parylene-parylene bonding to define channel features. Although the processes for forming devices, such as shown in FIG. 3, are described with reference to use of a single mask, one or more additional masks may be used. For example additional masks may be used to further define the features described, or to define additional features such as electrodes or electrode arrays or other features as may be apparent to one skilled in the art. Additionally, photoresist layers may be used and also parylene-parylene bonding may be used where desired for certain device features, whether formed during or after the processed described herein.

Figure 7:
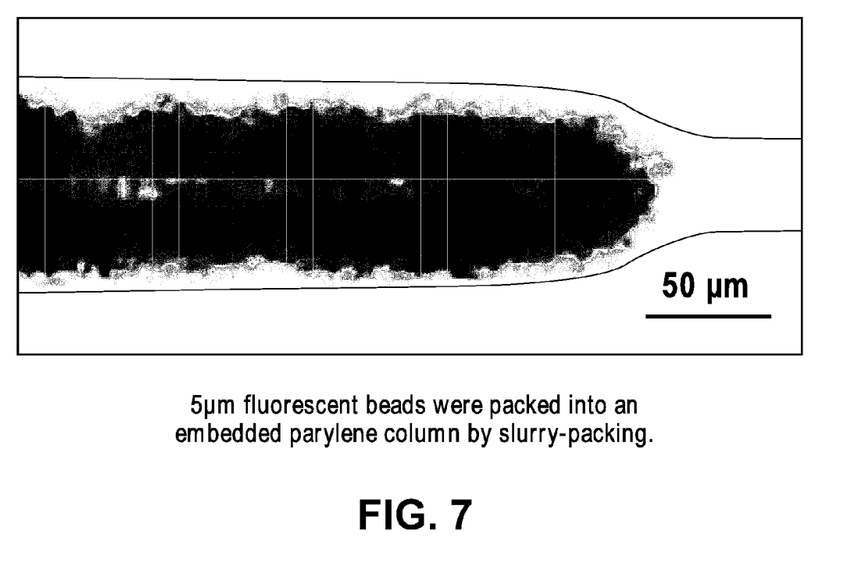
FIG. 7 illustrates an example of 5 μm fluorescent beads packed into an embedded parylene column by slurry-packing.
Figure 8:
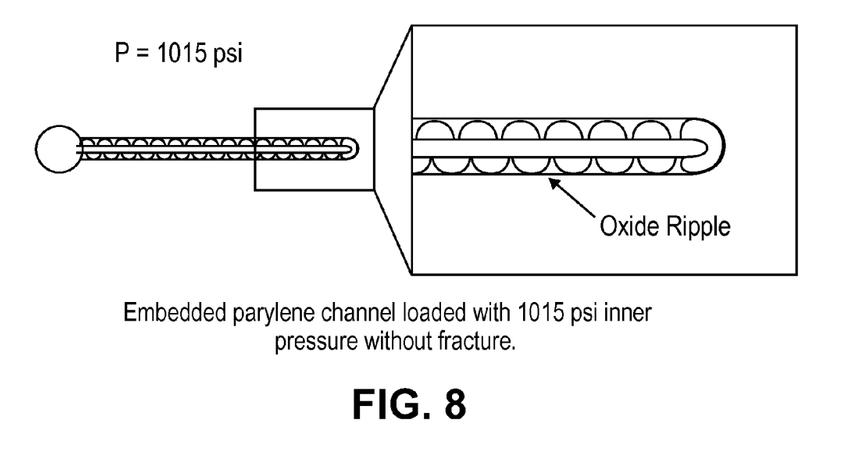
FIG. 8 illustrates an embedded parylene channel loaded with 1015 psi inner pressure without fracture.
Figure 9A:
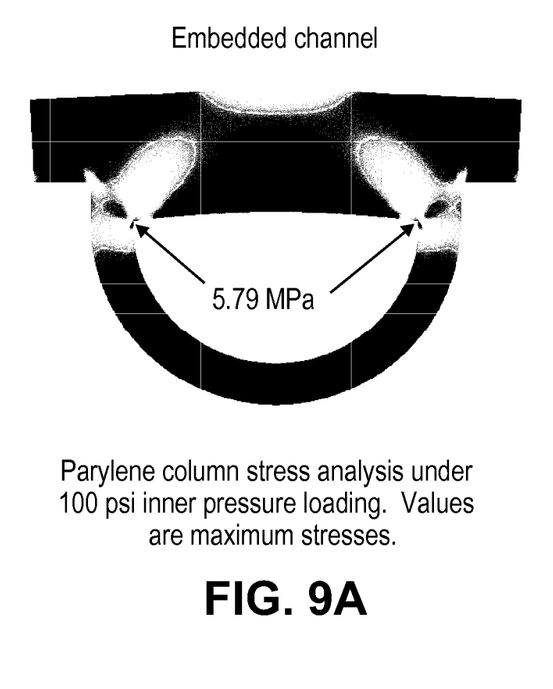
FIG. 9 illustrates parylene column stress analysis for (a) an embedded channel structure, and (b) a freestanding channel structure.
Figure 9B:
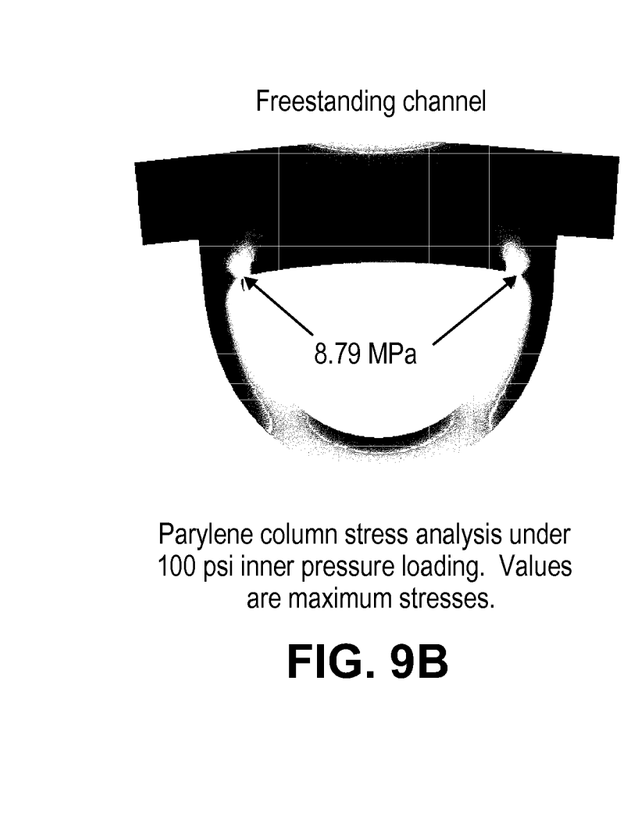
Figure 10:
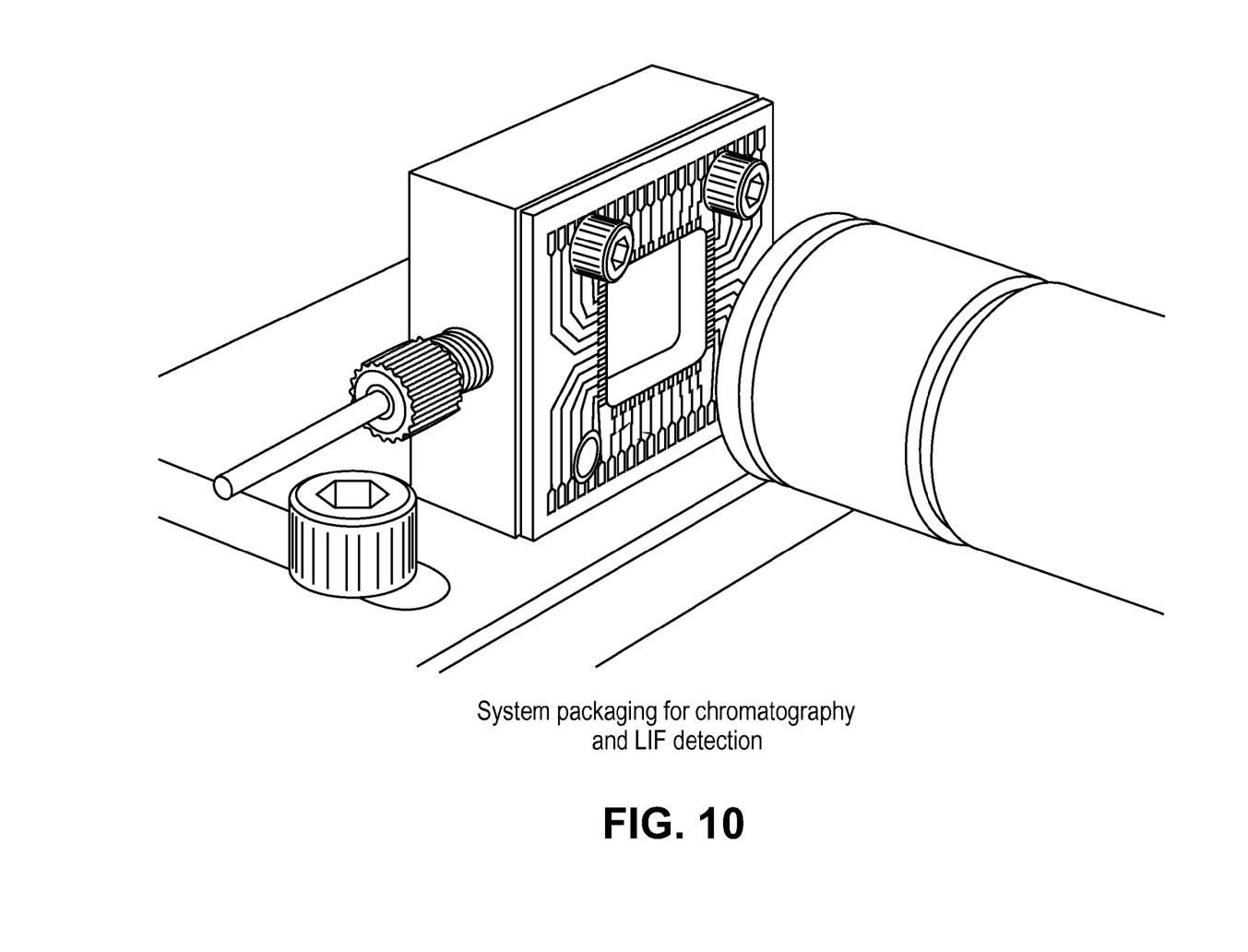
FIG. 10 illustrates a system package useful for chromatography and LIF detection applications.

As one example, with an optimized filter structure as shown in FIG. 7, 5 μm stationary-phase beads were successfully packed into a separation column via a conventional slurry-packing technique. Pressure capacity of an exemplary fabricated device was also studied. As shown in FIG. 8, testing results showed that an embedded parylene channel withstood at least 1000 psi without fracture, which is advantageous for on-chip chromatography applications. Such pressure capacity has not been achieved by non-embedded MEMS HPLC technology. Stress distribution in the parylene column wall under inner pressure loading was analyzed by FEMLAB simulation. The simulation, as shown in FIG. 9, showed the embedded-channel boundary condition reduced the maximum stress by 34% compared with a freestanding channel boundary condition. FIG. 3c illustrates an embedded parylene channel; FIG. 3b illustrates a thin film HPLC device that has been peeled away, or otherwise removed, from a substrate. The HPLC device of FIG. 3b includes a plurality of freestanding parylene channels and other features. FIG. 10 shows an example of a system package useful for chromatography and LIF detection applications.

Applications

The systems and methods of the present invention may be adapted to analyze a wide range of analytes in real time for a variety of applications. One specific embodiment of the present invention is a portable integrated microfluidic chip-based HPLC system that can be used to identify and analyze analytes in real time. The present systems provide a significant advantage over conventional HPLC systems have been used to identify and analyze analytes, such as harmful cyanobacteria water blooms, because such systems require a large sample to be taken and transported to the laboratory in order to obtain any meaningful results.

Target analytes that may be monitored and recorded using the present systems include, but are not limited to, dissolved gases, metals, ions and salts. Specific analytes include, but are not limited to, oxygen, sulfide, iron (including dissolved (ferrous) iron), manganese, acetate, propionate, butylrate, lactate, formate, glucose, hydrogen sulfide, dissolved carbon dioxide, ammonia, methane, hydrogen, sulfate and nitrate. The systems may also be adapted to detect the pH level of a given sample.

In one embodiment, the instrument is made to analyze water samples, such as those collected from oceans, rivers, aqueducts, or households. The system may be utilized to test for the presence of harmful compounds or contaminants. For example, there is increasing global concern that toxic cyanobacteria are impairing animal and human health. Therefore, in one embodiment the present system would be adapted to test for the presence of cyanobacteria.

Another embodiment of the invention provides a system for monitoring food quality. In the United States alone, it is estimated that approximately 1.4 million people get salmonella poisoning every year. Yet, an instrument for real time analysis of pathogen detection in foods has not yet been developed. The present invention provides the first microfluidic chip-based HPLC instrument that can detect in real time harmful pathogens in foods.

Another embodiment of the invention provides a system to analyze biological samples, such as bodily fluids, including urine, blood, and saliva. When a sample of body fluid is taken from a patient, it is usually sent to a laboratory to be tested. The results are generally not available for hours or even days. Further, because tests are largely based on physiological and systemic changes rather than local or cellular changes, results are inconclusive if there is not enough sample or if a particular disease is at an early stage. Consequently, disease is often not diagnosed until long after it has taken hold of the body. An instrument for real time analysis of relevant biological markers has not yet been developed. One embodiment of the present invention provides a microfluidic chip-based HPLC instrument that can detect in real time different biological markers in bodily fluids. For example, the system can be used to analyze blood chemistries, cholesterol, blood counts, or thyroid markers. Examples of analytes include glucose (serum), uric acid (serum), BUN, Creatinine (serum), BUN/Creatinine Ratio, sodium (serum), potassium (serum), chloride (serum), carbon dioxide (total), calcium (serum), phosphorous (serum), protein (total, serum), albumin (serum), Globulin (total), A/G ratio, bilirubin (total), alkaline phosphatases (serum), LDH, AST (SGOT), ALT (SGPT), GGT, and Iron (serum). Exemplary lipid analysis includes cholesterol (total), triglycerides, HDL cholesterol, and LDL cholesterol calc. Thyroid-related analysis includes, for example, TSH, Thyroxine (T4), T3 Uptake, and the free Thyroxine Index. Additional analysis includes white blood cell count, red blood cell count, hemoglobin, hematocrit, MCV, MCH, MCHC, RDW, platelets, polys, Lymphs, Monocytes, Eos, Basos, Polys (absolute), Lymphs (absolute), Monocytes (absolute), Eos (absolute value), and baso (absolute).

In another embodiment, the system is embodied in a portable instrument that can be used for various applications such as for wellness testing in household or clinics. For example, the system can perform testing of vitamin levels.

In the case where content in a cell is of interest, cell lysis can be performed on the chip by integrating a cell lysis device into the chip. Suitable cell lysis devices and methods for building them into a microfluidic chip are described in U.S. Pat. No. 6,287,831, Cell Lysis Device, U.S. Pat. No. 6,534,295, Cell Lysis Device, and U.S. nonprovisional application Ser. No. 10/391,993 filed Mar. 18, 2003, Cell Lysis Device (issued Feb. 13, 2007 as U.S. Pat. No. 7,176,018), the entire disclosures of which are incorporated herein by reference.

In another embodiment, the system provides an instrument used in the process of drug discovery. For example, the system may be used separate and detect proteins to identify new drug targets, and it can be used to study drug metabolism.

In some embodiments, the separation columns on the integrated microfluidic chip provide for sample preparation as well as analyte separation. This is advantageous because preparing an analytical sample for conventional HPLC involves several steps and bulky equipment. In contrast, the present system provides a compact system that may include one or more components for filtration and/or storage for automated sample preparation. In one embodiment, blood filtration can be performed to separate blood cells from plasma. For example, the separation column itself can act like a filter for blood cells. In many cases, targets of interest are often in low concentration in the presence of much abundant contaminates or substances. In these cases, the columns may be used to enrich or pre-concentration analytes by using columns packed with certain types of beads. In addition packed column with functionalized beads may be very useful for filtering out contaminates or other unwanted substances. For example, reverse-phase column can be used to retain large proteins while allowing small ions to pass through.

The invention has been described with reference to various specific and illustrative embodiments. However, it should be understood that many variations and modifications may be made while remaining within the spirit and scope of the following claims.

What is claimed is:

1. An integrated microfluidic liquid chromatography device comprising:
   a substrate having a surface;
   at least two separation columns each having an inlet and an outlet, the at least two separation columns integrated into the substrate surface and adapted to perform separate and simultaneous chromatographic separations on at least two different samples, the chromatographic separations being of different types, at least one of the separation columns formed by depositing, using chemical vapor deposition (CVD), a polymer over neighboring etched regions of the substrate, one etched region being narrower and one etched region being wider, the depositing sufficient to coat a portion of a bottom of and seal over the narrower etched region and define an inner channel and then coat an inner surface of the inner channel from the polymer diffusing through the wider region until the wider etched region is sealed over by the deposition; and
   a detector array comprising at least two sample detectors integrated into the substrate surface and in fluid communication with the outlet of the at least two separation columns.

2. The device of claim 1 wherein the at least two separation columns adapted to perform chromatographic separations of different types are formed by a single mask process.

3. A microfluidic system for sample analysis comprising:
   a reservoir assembly comprising at least two sample reservoirs;
   an integrated microfluidic chromatography device in fluid communication with the at least two sample reservoirs, the integrated microfluidic chromatography device comprising at least two separation columns integrated into a substrate and adapted to perform separate and simultaneous separations of samples, the separations being of different types, and at least one detector integrated into the substrate, at least one of the separation columns formed by depositing, using chemical vapor deposition (CVD), a polymer over neighboring etched regions of the substrate, one region being narrower and one region being wider, the depositing sufficient to line a portion of a bottom of and seal over the narrower etched region and define an inner channel and then coat an inner surface of the inner channel from the polymer diffusing through the wider region until the wider etched region is sealed over by the deposition;
   a pump adapted to deliver samples from the at least two sample reservoirs to the integrated microfluidic chromatography device;
   an analyte detection assembly comprising at least one detector in fluid communication with at least one separation column of the at least two separation columns; and
   a processing unit in electrical communication with the at least one detector.

4. A method for detecting an analyte in a sample, the method comprising passing the sample through the system of claim 3.

5. A microfluidic chromatography device comprising:
   an integrated column and inlet/outlet port formed by depositing, through chemical vapor deposition (CVD), a polymer over a surface of a substrate that has been etched with narrower and wider surface openings that are connected, the CVD coating a portion of a bottom of and sealing over the narrower opening to define an inner surface of the column, the column further formed by further CVD of the polymer such that the polymer enters the column through the connected wider surface opening, which defines the inlet/outlet port, and coats the inner surface of the column, and then the column and inlet/outlet port are peeled from the substrate.

6. An integrated microfluidic chromatography device comprising:
   a filter; and
   a separation column in fluid communication with the filter, wherein the filter and separation column were formed by depositing a polymer over an open etched channel of a substrate, the channel having regions, one etched region being narrower and another etched region being wider, the depositing sufficient to coat a portion of a bottom of and seal over the narrower etched region to define an inner channel for the filter and then coat an inner surface of the inner channel from an opening to the wider etched region until the wider etched region is sealed over to define the separation column.

7. The device of claim 6 wherein the device is further processed by peeling the filter and separation column from the substrate.

8. The device of claim 6 wherein the separation column comprises a cation exchange chromatographic separation column or an anion exchange chromatographic separation column.

9. The device of claim 6 wherein the separation column is a reverse-phase liquid chromatographic separation column or an ion-exchange chromatographic separation column.

10. The device of claim 6 wherein the substrate comprised silicon, glass, plastic or metal.

11. The device of claim 10 wherein the substrate includes a silicon wafer.

12. The device of claim 6 wherein the separation column is characterized by a column diameter of no more than about 200 microns.

13. The device of claim 6 wherein the separation column is characterized by a column diameter of no more than about 100 microns.

14. The device of claim 6 wherein the polymer is parylene.

15. The device of claim 6, further comprising one or more sample detectors in fluid communication with the separation column.

16. The device of claim 15 wherein the one or more sample detectors are microscale or nanoscale detectors integrated into the substrate.

17. The device of claim 6 wherein the separation column is packed with a solid phase comprising nanoscale or microscale beads.

18. The device of claim 6 wherein the separation column is packed with a solid phase comprising a monolith solid phase.

19. The device of claim 6, further comprising one or more additional separation columns integrated into the substrate.

20. The device of claim 19 wherein each of the separation columns integrated into the substrate is adapted to perform a different type of chromatographic separation.

\* \* \* \* \*